(12) United States Patent
Naoto et al.

(10) Patent No.: US 8,317,766 B2
(45) Date of Patent: Nov. 27, 2012

(54) INDIVIDUALLY PACKAGED ABSORBENT ARTICLE

(75) Inventors: Nakao Naoto, Shinjyuku-ku (JP); Kume Yukio, Shinjyuku-ku (JP)

(73) Assignee: Daio Paper Corporation, Shikokuchuo-shi (JP)

( * ) Notice: Subject to any disclaimer, the term of this patent is extended or adjusted under 35 U.S.C. 154(b) by 438 days.

(21) Appl. No.: 12/666,996

(22) PCT Filed: Jun. 27, 2008

(86) PCT No.: PCT/JP2008/061717
§ 371 (c)(1),
(2), (4) Date: Dec. 28, 2009

(87) PCT Pub. No.: WO2009/001922
PCT Pub. Date: Dec. 31, 2008

(65) Prior Publication Data
US 2010/0324518 A1    Dec. 23, 2010

(30) Foreign Application Priority Data
Jun. 28, 2007    (JP) ................................. 2007-170871

(51) Int. Cl.
*A61F 13/15*    (2006.01)
(52) U.S. Cl. ............................. 604/385.02; 604/385.201
(58) Field of Classification Search ............. 604/385.02, 604/385.201
See application file for complete search history.

(56) References Cited

U.S. PATENT DOCUMENTS

| | | | |
|---|---|---|---|
| 2001/0003152 A1* | 6/2001 | Lee | 604/385.02 |
| 2002/0183709 A1* | 12/2002 | Munsch | 604/385.05 |
| 2003/0069556 A1* | 4/2003 | Costa | 604/385.02 |

FOREIGN PATENT DOCUMENTS

| | | |
|---|---|---|
| JP | 9-266928 | 10/1997 |
| JP | 2000-325393 | 11/2000 |
| JP | 2006-340978 | 12/2006 |

* cited by examiner

*Primary Examiner* — Lynne Anderson
*Assistant Examiner* — Kathryn D Sheikh
(74) *Attorney, Agent, or Firm* — Jordan and Hamburg LLP

(57) ABSTRACT

In order to produce an easily removable individually packaged absorbent article such as a sanitary napkin, while maintaining the surface sheet thereof in a hygienic state and avoiding the occurrence of individually-packaging failures such as bending or wrinkling of a packaging sheet on the production line, in the process of producing individually packaged absorbent articles, absorbent articles are provided at definite intervals on a band shaped sheet and a notch out satisfying the following conditions is formed at the intermediate site between each pair of the absorbent articles. [1] The notch out is formed by an outward curved cut line, which starts from the cutting-starting point in the side periphery toward the diagonally tilting direction forward in the line and shows a convex outward of the band shaped sheet, and an inward curved line which is connected to the endpoint of the outward curved cut line via a ininflexion point P and shows a convex inward of the band shaped sheet. [2] When the interval distance in the line direction of the outward curved cut line is referred to as B and the distance from the ininflexion point P to the side periphery line of the band shaped sheet is referred to as A, the relationship B>1.5A is satisfied.

5 Claims, 14 Drawing Sheets

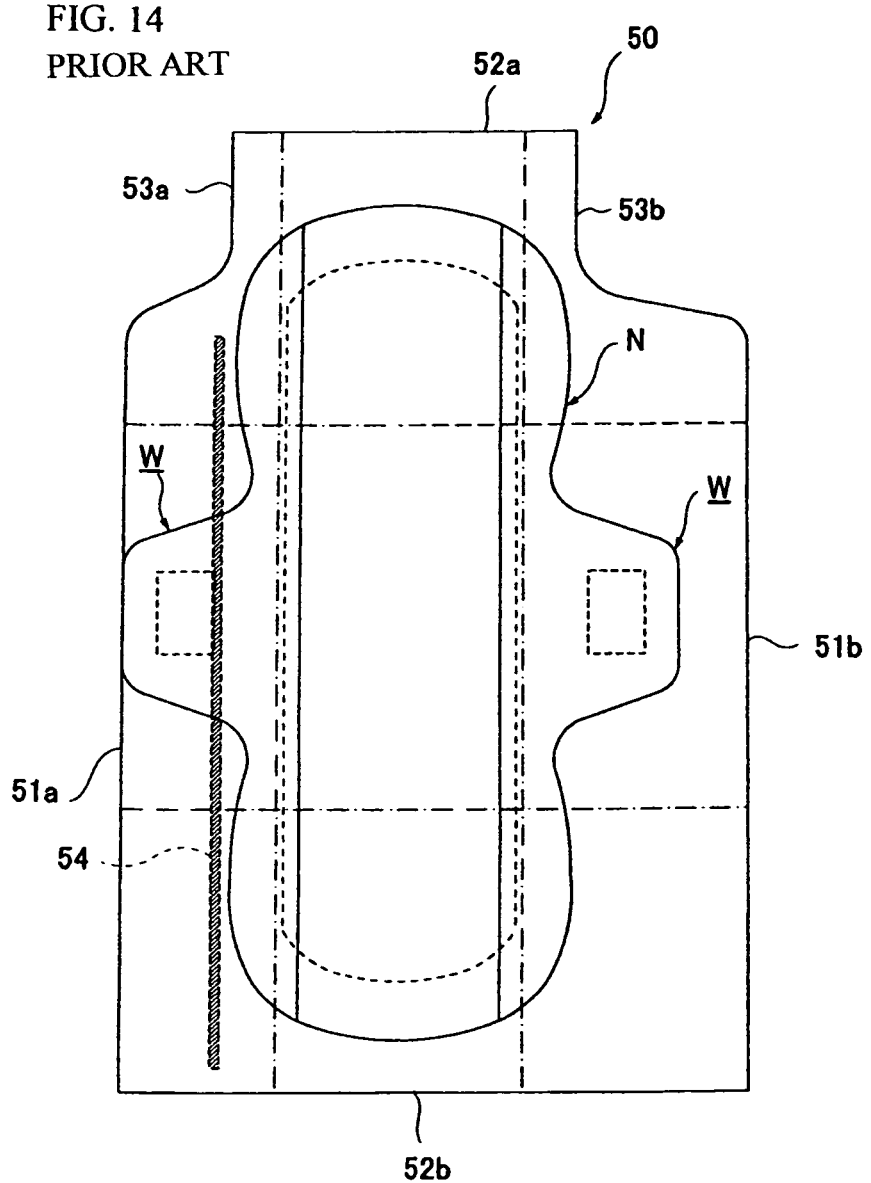

INDIVIDUALLY PACKAGED ABSORBENT ARTICLE

BACKGROUND OF THE INVENTION

The invention relates to an individually packaged absorbent article individually packaged by a package sheet.

Conventionally, as an absorbent article such as a sanitary napkin, a pantiliner, a sheet for vaginal discharges, and a pad for urinary incontinence, an article containing absorbers made of cotton like pulps between a liquid-impermeable back sheet consisting of a polyethylene sheet or a polyethylene laminated nonwoven fabrics and the like, and a liquid-permeable surface sheet consisting of a nonwoven fabric or porous plastic sheet and the like are known.

In this kind of an absorbent article, it is intended to prevent displacement of the article when worn by providing one or multiple adhesive layers, for example, at the non-skin contact face side (outer face of the liquid-impermeable back sheet), and in the case where wing shape flaps extending outward from both side edges in a longitudinal direction of the napkin body is formed in an integrated manner, it is intended to provide an adhesive layer at the face (outer face) of the liquid-impermeable back sheet side of the wing shape flap.

When said absorbent articles are individually packaged, said adhesive layer is covered by a release sheet consisting of a paper or a film, and a package sheet is placed on the outer face side of the absorbent article at the same time, and the napkin, the release sheet and the package sheet are folded together in three or four in a longitudinal direction, and then, the side edge section is sealed by heating, and the opening section is sealed by a tag tape and the like.

However, in the above-mentioned packaging style, due to the protrusion of a tab for heat-sealing to the side direction, there arises problems that compactification cannot be realized and that both the release sheet and the package sheet generate waste at the time of use which results in wastefulness of natural resources.

Then, in recent years, as the individually packaged structure for realizing compactification while eliminating said release sheet, many kinds of structures in which the napkin body is directly packed by a package sheet are proposed. For example, in the patent document 1, an individually packaged absorbent article as follows is disclosed; as shown in FIGS. 14 to 16, a package sheet 50 is a substantially rectangular sheet defined by the matched pair longitudinal side edges 51*a*, 51*b* corresponding to the longitudinal direction of the absorbent article N and the matched pair lateral side edges 52*a*, 52*b* corresponding to the lateral direction of the absorbent article N. The release treatment is provided in a region at least corresponding to the adhesive layer for stopping the disagreement at a contact face on the absorbent article side, and at the same time, in at least one side of said lateral side edges 52*a*, 52*b*, notch cut outs 53*a*, 53*b* are formed by cutting the corner where the longitudinal side edges 51*a*, 51*b* and lateral side edge 52*a* are crossing, placing the absorbent article body on the release treatment side of said package sheet 50, folding both side sections of the longitudinal side edges 51*a*, 51*b* of a package sheet 50 to a liquid-permeable surface sheet side subsequently. In this folding condition, from said notch cut outs 53*a*, 53*b*, a part of the absorbent article N containing the end section of the absorber is made to be presented to the outside, and at the overlapping tab section of the both side sections of the longitudinal side edges 51*a*, 51*b*, both side sections of said longitudinal side edges 51*a*, 51*b* are releasably bonded by the line shape adhesive 54 provided following the longitudinal direction starting from the position located towards the central side from the end section of said absorber. Further, a package sheet and an absorbent article are subsequently folded together in a longitudinal direction and sealed.

Citation List

Patent Document 1: Unexamined patent publication No. 2006-340978

SUMMARY OF THE INVENTION

According to the individually packaged absorbent article described in said Patent Document 1, at the time of use, when the folding in a longitudinal direction of the absorbent article N and the package sheet 50 is released to be a development state, from the opening section formed by the notch cut outs 53*a*, 53*b*, a part of the absorbent article N including the edge section of the absorber is made to be presented to the outside, and when the absorbent article N is pulled so that it is released from the package sheet 50 by gripping the end section of the absorber between thumb and forefinger, both side sections of the longitudinal side edges 51*a*, 51*b* are developed, while the line shape adhesive 54 bonding both side sections of the longitudinal side edges 51*a*, 51*b* of the package sheet 50 together are being released, and said absorbent article N can be easily taken out from the package sheet 50. On the occasion of the release of the absorbent article N, by releasing ones grip on the end section of the absorber, it is possible to utilize the force of the absorber having the rigidity to some extent and so it is possible to develop easily both side sections of the longitudinal side edges 51*a*, 51*b* against the adhesive force of the line shape adhesive 54. In addition, said line shape adhesive 54 is provided in a longitudinal direction starting at the position located toward the central side from the end section of the absorber and is set to be resistant in a state where the edge section of the absorber is released to some extent, and so it becomes possible to be released easily from the edge of the paper.

Further, said line shape adhesive 54 joins both side sections of the longitudinal side edges 51*a*, 51*b* of the package sheet 50 firmly, decreases inconvenience of the individually packaged absorbent article.

However, in the production of said individually packaged absorbent article, as shown in the FIG. 17, after forming nearly U shape notch cut outs 53*a*, 53*b* from the side edge towards the internal side at a predetermined interval against the continuing strip sheet in the line direction, the absorbent article N was placed in each individually packaged sheet, and after both side sections of the longitudinal side edges 51*a*, 51*b* of the package sheet 50 is subsequently folded to the side of the liquid-permeable surface sheet, the package sheet 50 and the absorbent article N are subsequently folded together in a longitudinal direction. However, there were inconvenient cases where the side edge section (diagonal line section 55) of said nearly U shape notch cut outs 53*a*, 53*b* are folded back to the opposite side or got wrinkles during steps in the production line. In addition, since the exposure area of the end section of the absorber body presented from said notch cut outs 53*a*, 53*b* is large, there was a problem such as a concern about producing waste.

Then, a main object of the invention is to suppress the generated amount of waste by eliminating the release sheet and to provide an individually packaged absorbent article: which can be accommodated in a compactly folded absorbent state; and further the surface sheet is kept in a hygienic state, while enabling convenient taking-out of the napkin and the inconvenience of the individual package such as folding back or getting wrinkles of the package sheet generated during the production line is avoided.

An individually packaged absorbent article is provided, consisting of an absorbent article including an absorber between a liquid-permeable surface sheet and a back face sheet in which an adhesive layer for preventing displacement of the absorbent article is formed on said outer face of the back face sheet and a package sheet which individually package the absorbent article as a first aspect of the invention for solving said problem, wherein in the production step of said individually packaged absorbent article, said package sheet runs out as a continuous band sheet in the line direction, and at the side edge section on at least one side of the intermediate section where the absorbent articles are placed at a predetermined interval, a notch cut out section which satisfies the following conditions (1) and (2):

(1) said notch cut out section is formed by the outward curved cut line in a shape bulging to the outside of the band sheet toward the slanted forehand inclined direction of the line front from the cut start point of the side section, the inward curved cut line which continues from the terminal end of said outward curved cut line through the inflexion point, and is in a shape bulging to the inside of the band shape sheet, and the cut shape line in a nearly longitudinally half cut drop shape which continues from the inward curved cut line, and extends to the width direction of the band sheet to reach the cut terminal point of the side edge section.

(2) when the sectional distance in the line direction of the outward curved cut line in the line direction is referred to as B and the distance from the inflexion point to the side edge line of the band sheet is referred to as A, the relationship B>1.5A is to be satisfied.

wherein the package sheet is cut into each package sheet having the matched pair longitudinal side edge corresponding to the longitudinal direction of the absorbent article and the matched pair lateral side edge corresponding to the lateral direction of the absorbent article by a cut line following the width direction of the band sheet from said inside of the section of the outward curved cut line and the inward curved cut line, and at the contact face on the absorbent article side, the release treatment is provided in the region corresponding to at least said adhesive layer region, wherein in a state where the absorbent article is placed at the processing face side of the release treatment of said package sheet, both side sections on the longitudinal side edge side of said package sheet are sequentially folded to the liquid-permeable surface sheet side, and in this folding state, the front end section of the absorbent article is made to be presented to the outside from said notch cut out section, in the overlapping tab section of on both side sections on the longitudinal side edge side of longitudinal side edge side are releasably bonded by the line shape adhesive provided following the longitudinal direction, and further the package sheet and the absorbent article are sequentially folded together in the longitudinal direction and sealed by the tab tape.

In the production step of the individually packaged absorbent article according to the above first aspect of the invention, firstly the package sheet runs out as the continuous band sheet in the line direction and the absorbent article is placed at determined interval. In the intermediate section, the notch cut out satisfying the following two conditions is formed.

As the first condition, the outward curved cut line in a shape bulging to the outside of the band sheet toward the slanted forehand inclined direction of the line front from the cut start point of the side edge section, and the inward curved cut line which continues from the terminal end of said outward curved cut line through the inflexion point and is in a shape bulging to the inside of the band shape sheet are formed. And said notch cut out section is formed by the cut shape line in a nearly longitudinally half cut drop shape which continues from the inward curved cut line, and extends to the width direction of the band sheet to reach the cut terminal point of the side edge section.

In addition, as the second condition, when the sectional distance of the outward curved cut line in the line direction is referred to as B and the distance from said inflexion point to the side edge line is referred to as A, the condition B>1.5A is satisfied.

The package sheet having a notch cut out satisfying these conditions can produce an individually packaged absorbent article without causing inconvenience such as folding back of the side edge section of the notch cut out or getting wrinkles during the steps through the production line.

In addition, since the front end section of the absorbent article is made to be presented to the outside from the opening section formed by the notch cut out satisfying said first and second conditions, when the front end section of the absorbent article is pulled by gripping it so that it is released from the package sheet, both side sections of the longitudinal side edge are developed, while the line shape adhesive bonding both side sections of the longitudinal side edges of the package sheet is being released, and the absorbent article can be easily taken out from the package sheet.

In addition, said notch cut out is formed in the minimum requirement nearly following the outer size of a finger by the cut shape line in a nearly longitudinally half cut drop shape, and so almost no penetration of dusts occurs and it becomes possible to keep the surface sheet of the napkin in a hygienic state.

In addition, on the contact face of the absorbent article of the package sheet, the release treatment is provided at least in the region corresponding to the adhesive layer region for stopping the disagreement, and so it is possible to eliminate the release sheet and suppress the generated amount of the extra dusts. In addition, since the absorbent article body is placed on the processing face side of the release treatment, and the individually packaged absorbent article is formed by folding both side sections on the longitudinal side edge side of the package sheet to the liquid-permeable surface sheet side, it becomes possible to accommodate the absorbent article by folding it in compact.

As a second aspect of the invention, the individually packaged absorbent article according to the first aspect of the invention satisfying the relationship C/(B+C)=0.2~0.5, when the sectional distance of said outward curved cut line in the line direction is referred to as B and the sectional distance of said inward curved cut line in the line direction is referred to as C, is provided.

The before-mentioned sectional distance of the inward curved cut line in the line direction C is preferably 0.2~0.5 of the sectional distance (B+C) of the outward and the inward curved cut line.

As a third aspect of the invention, the individually packaged absorbent article according to the first or second aspect of the invention, wherein in said absorbent article, a wing shape flap which is protruding toward the side from the longitudinal direction side edge section and is fixed in a manner to catch up the crotch section of the underwear at wearing is provided, and an adhesive layer for stopping displacement of the wing shape flap is provided on the face of said liquid-impermeable back sheet side of the wing shape flap, and when both side sections on the longitudinal side edge side of said package sheet is folded sequentially to the liquid-permeable surface sheet side, said wing shape flap is to be folded to the liquid-permeable surface sheet side.

The above described invention according to the third aspect thereof individually packages the absorbent article having a wing shape flap protruding from the longitudinal direction side edge section of the absorbent article, and in this case, it is preferred that said wing shape flap is folded to the liquid-permeable surface sheet side when both side sections on the longitudinal side edge side of the package sheet is folded.

As the invention according to a fourth aspect thereat the individually packaged absorbent article according to any of the first to third aspects of the invention is provided, wherein the above-mentioned line shape adhesive is the continuous line shape adhesive or intermittent line shape adhesive.

Said line shape adhesive may be either in a continuous line shape or in an intermittent line shape.

As the invention according to a fifth aspect thereof, the individually packaged absorbent article according to any of the first to fourth aspects of the invention is provided, wherein at the stage when the absorbent article is placed on the package sheet and both side sections on the longitudinal side edge side of the package sheet is folded sequentially to the liquid-permeable surface sheet side, the heat-sealing is applied in both end sides in the longitudinal direction.

In the invention according to the above mentioned fifth aspect thereof, at the stage when the absorbent article is placed on the package sheet and both side sections on the longitudinal side edge side of the package sheet are folded sequentially to the liquid-permeable surface sheet side, the heat-sealing is applied at both end section in the longitudinal direction, and therefore the absorbent article can be kept in a hygienic state, and since they are fixed in folding state of the package sheet, they can be folded firmly because the package does not collapse.

As explained above in detail, according to the invention, the release sheet can be eliminated to suppress the generation of extra waste, and it is also possible to accommodate the compactly folded absorbent article. In addition, the surface sheet can be kept in hygienic state, while making it possible to take out the napkin conveniently, and inconvenience of the individual packaging such as folding back of the package sheet, getting wrinkles and the like generated during production line can be removed.

BRIEF DESCRIPTION OF THE DRAWINGS

FIG. 14 is a development view of the conventional sanitary napkin N;

DETAILED DESCRIPTION OF THE INVENTION

Figure 1:
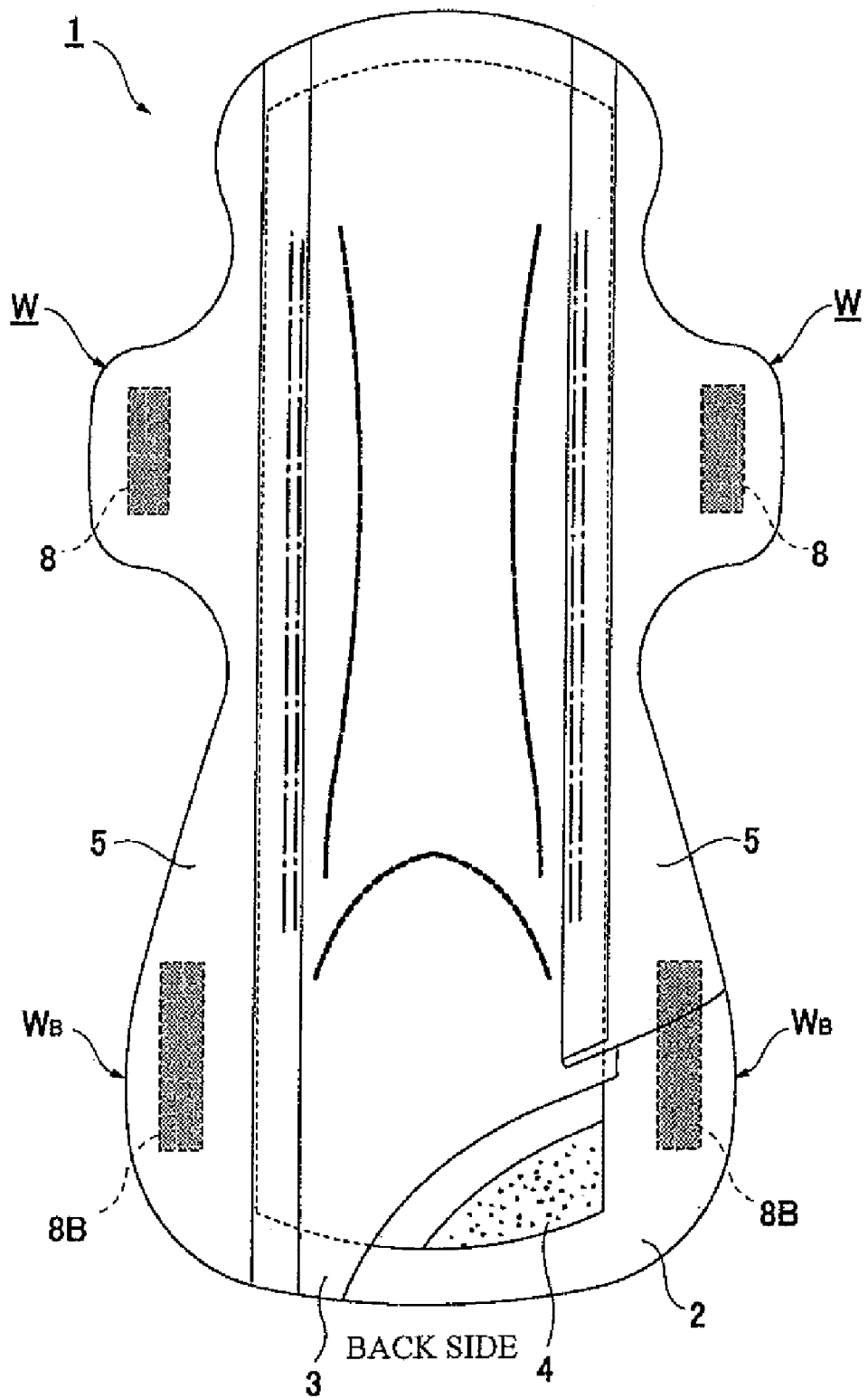
FIG. 1 is a partially ruptured development view of a sanitary napkin 1 according to the invention.

An embodiment of the invention will be explained below in detail with reference to the drawings.

Said sanitary napkin 1 is composed of a liquid-impermeable back sheet 2 consisting of a polyethylene sheet, polypropylene sheet and the like, a liquid-permeable surface sheet 3 which can pass the menstrual blood and vaginal discharges, an absorber 4 consisting of cotton pulp, synthetic pulp and the like which is sandwiched between these sheets and the side nonwoven fabrics 5,5 formed on both side sections following the longitudinal direction respectively, and in the longitudinal direction side edge section of the napkin 1, the wing shape flaps W,W are formed which protrude to the side direction by the section where said back face sheet 2 and the side nonwoven fabric 5 are mutually adhered and which are fixed in a manner of catching up the crotch section of the underwear at wearing, and the second wing shape flaps $W_B$, $W_B$ are formed at the position located towards the buttocks side from the first flap. Here, said absorber 4 can be surrounded by a crepe paper in order to keep the shape and to improve the diffusivity.

In the circumference of said absorber 4, at the top and bottom end edge sections thereof, the outer edge section of said liquid-impermeable back sheet 2 and the liquid-permeable surface sheet 3 are bonded by adhesive means such as an adhesive or heat-sealing, and at both side edges, said liquid-impermeable back sheet 2 and said side nonwoven fabric 5 which are extending to the side direction from the absorber 4 are bonded by the adhesive means such as hot-melt or heat-sealing.

Further, the structure of said sanitary napkin 1 will be explained below in detail. For said liquid-impermeable back sheet 2, a waterproof sheet material such an olefin resin sheet and the like including polyethylene and polypropylene is used, and in addition to this, the laminated nonwoven fabric produced by laminating nonwoven fabric on the polyethylene sheet and the like, and furthermore after assuring substantial liquid-impermeability, a nonwoven fabric sheet(in this case, the liquid-impermeable back sheet is constituted by the waterproof film and the nonwoven fabric) and the like can be used. In recent years, from the view point of prevention of the absorbent article feeling damp against the wearer's body, there is a tendency to use a material having moisture permeability (i.e., permeability to water vapor). This waterproof and moisture permeable material is a micro porous sheet obtained by the mono or biaxial-orientation of the sheet formed by melting and kneading of polyethylene and polypropylene mixed with inorganic fillers.

Then, as said liquid-permeable surface sheet 3, a porous or non-porous nonwoven fabric and a porous plastic sheet and the like are preferably used. The material fiber constituting the nonwoven fabric may be, for example, synthetic fibers such as olefin type including polyethylene, polypropylene and the like, polyester type and polyamide type and the like, and in addition the regenerated fiber such as rayon, cupra and the like, and the natural fibers such as cotton, and nonwoven fabric obtained by an appropriate processing method such as spunlacing, spunbonding, thermalbonding, melt blowing, needle punching and the like can be used. Among these processing methods, spunlacing is excellent in flexibility, spunbonding in drape property, and thermalbonding and airthrough are bulky and soft.

The absorber 4 placed between said liquid-impermeable back sheet 2 and the liquid-permeable surface sheet 3 is, for example, constituted by flat shape pulp and water absorptive polymer. Said water absorptive polymer is mixed in the pulp constituting the absorber as, for example, particulate powder. The pulp may be the chemical pulp obtained from wood, cellulose fibers such as dissolved pulp and artificial cellulose fibers such as rayon, acetate and the like. The softwood pulp having a long fiber length is more preferable than the hardwood pulp with respect to the function and price. As is the case of the example, when a crepe paper surrounding the absorber 4 is provided, a crepe paper is placed between the liquid-permeable surface sheet 3 and the absorber 4 and, as a result, the body fluid is diffused rapidly by said crepe paper, which is excellent in absorbability, and reverse flow of the menstrual blood is prevented.

On the other hand, on both sides of the sanitary napkin 1 surface side, the side nonwoven fabrics 5,5 is provided over the nearly entire length of napkin 1 in the longitudinal direction, and a part of the side nonwoven fabrics 5,5 is extended to the side direction, and with a part of the liquid-impermeable back sheet 2 similarly extended to the side direction, the wing shape flaps W, W are formed, and whereby the second wing shape flaps $W_B$, $W_B$ are formed at the position located on the buttocks side.

As said side nonwoven fabric 5, according to the function to be treated as important, the nonwoven fabric subjected to the water-repellent treatment or the nonwoven fabric subjected to the hydrophilic treatment may be used. For example, if the function is to prevent the penetration of menstrual blood and vaginal discharges and the like or to improve the feeling of touch (tactility) is emphasized, it is preferable to use a nonwoven fabric subjected to the water repellent treatment by coating with a silicon type, a paraffin type, or alkylchromic chloride type water repellent. On the other hand, if the absorbability of the menstrual blood and the like in said wing shape flaps W,W is treated as important, it is preferable to make the nonwoven fabric swelled or porous either by a polymerization method conducted in the presence of a compound having a hydrophilic group, for example, an oxidation product of polyethylene glycol in the production process of the synthetic fiber or by a method to deposit metal hydroxide after treating by metal salt such as tin tetrachloride, dissolving the surface partially to make it porous and to use the nonwoven fabric subjected to the hydrophilic treatment provided with hydrophilicity due to capillarity.

Figure 2:
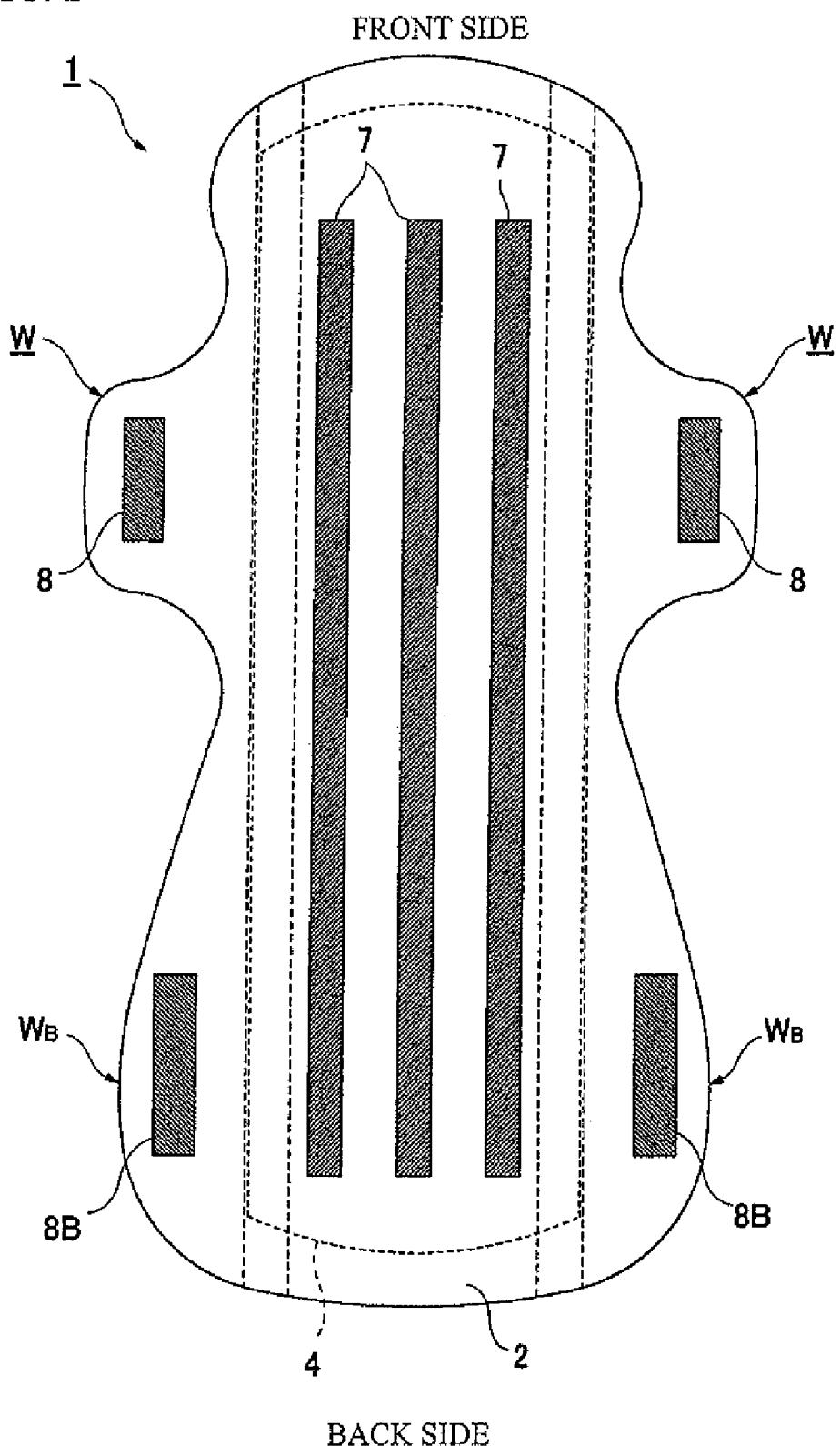
FIG. 2 is a back face view of FIG. 1.

As shown in FIG. 2, at the non-skin contact face of the body section where the absorber 4 is placed between said liquid-permeable surface sheet 3 and the liquid-impermeable back sheet 2, for fixing to the underwear, a plurality of the adhesive layers of an appropriate applying pattern, three layers of adhesive layers 7, 7 . . . for preventing displacement of the absorbent article in the example illustrated by the figure, is formed. In addition, on the face at the side of the liquid-impermeable back sheet 2 of said wing shape flaps W, W and the second wing shape flaps $W_B$, $W_B$, the adhesive layers 8, 8B . . . for stopping displacement of the wing are formed, respectively.

As the adhesive forming said adhesive layers 7, 8, 8B for preventing displacement, for example, the one whose main component is any of styrene type polymer, tackifier, and plasticizer is used preferably. As the styrene type polymer, styrene-ethylene-butylene-styrene block copolymer, styrene-butylene-styrene block copolymer, styrene-isobutylene-styrene copolymer, and the like can be mentioned. However, one kind of these polymers may be used or a polymer blend comprising two or more kinds of these polymers may be used. Among these, styrene-ethylene-butylene-styrene block copolymer is preferable because the heat-stability is excellent. In addition, as the aforementioned tackifier and the plasticizer the one which is a solid at an ambient temperature can be used preferably. As the tackifier, for example, C5 type petroleum resin, C9 type petroleum resin, dicyclopentadiene type petroleum resin, rosin type petroleum resin, polyterpene resin, terpenephenol resin, and the like can be mentioned. As said plasticizer, for example, in addition to the monomer type plasticizer such as biphenyl phosphate, dibutyl phthalate, dioctyl phthalate and the like, polymer type plasticizer such as vinylpolymer and polyester can be mentioned.

Figure 3:
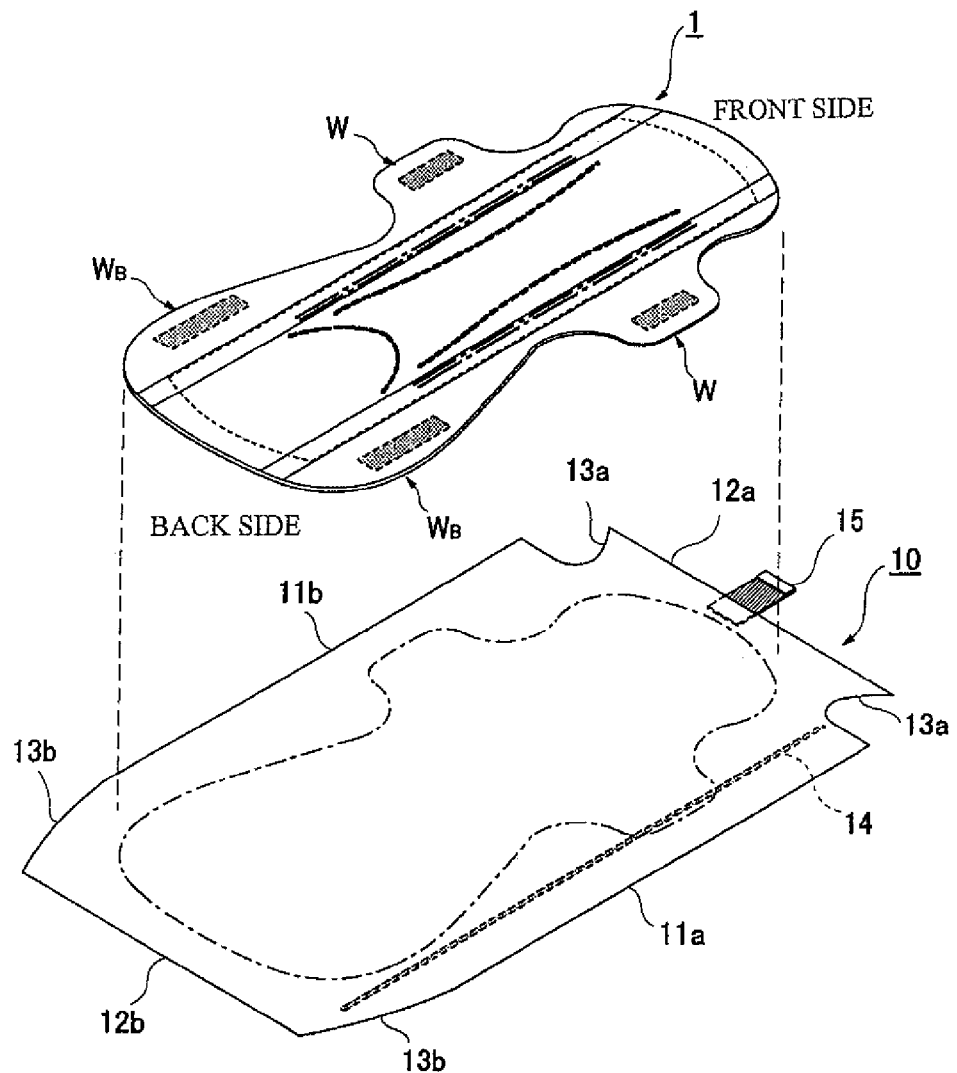
FIG. 3 is a separation view of the napkin 1 and the package sheet 10.

As shown in FIG. 3, the package sheet 10 which individually packages said sanitary napkin 1 is to be a nearly rectangular sheet defined by the matched pair longitudinal side edges 11a, 11b corresponding to the longitudinal direction of the napkin 1 and the matched pair lateral side edges 12a, 12b corresponding to the lateral direction of the napkin 1. As the material, a paper, a plastic film or the like can be used; however, it is preferable to use a thin and a highly flexible plastic film. As for the dimension, it is preferable to set the longitudinal dimension a bit longer than the total length of the napkin 1, to assure an extra length margin at the front and the rear of the napkin, and to set the lateral dimension a bit larger than the width dimension of the napkin 1 to assure an extra width margin at both lateral edges of the napkin 1.

It is acceptable if a partial release treatment is applied in the region at least corresponding to the region where said adhesive layers 7,7 for preventing displacement are formed in the contact face on the napkin 1 side of said package sheet 10. Here, in the example illustrated by the figure, the release treatment is applied on the entire face of the contact face on the napkin 1 side of the package sheet 10. In addition, the package sheet 10 and the remover(not shown) of another member may be bonded to set a release region. Said release treatment is performed by coating or spray coating of a release treatment liquid containing silicon type resin, fluorine type resin or tetrafluoroethylene type resin and the like. The example of said region where the release treatment is not applied is, for example, the region where the adhesive (a line shape adhesive) for bonding the package sheet 10 is present and the region where the adhesive for bonding said remover of another member is present.

In addition, in the vicinity of the longitudinal direction side edge on the outer side of said package sheet 10, a line shape adhesive 14 following the longitudinal direction is provided, and at nearly the center of the lateral direction side edge, the tag tape 15 is provided. Said line shape adhesive 14 is provided starting from the position located towards the central side from the absorber end section. Said tag tape 15 is a member consisting of a paper or a plastic film, and the base end side is bonded to the package sheet 10 unreleasably and a releasable adhesive layer is provided at the protruding section. Here, at the edge section of the protruding section, a non-adhesive gripping section may be formed.

In addition, on the lateral side edge 12a side on the mounting side of the tag tape 15, the notch cut outs 13a, 13a are formed respectively by cutting the corner in a predetermined shape where the longitudinal side edges 11a, 11b and lateral side edge 12a are crossing. In addition, in the lateral side edge 12b at the non-mounting side of the tag tape 15, the notch cut outs 13b, 13b are formed respectively by cutting the corner in a predetermined shape where the longitudinal side edges 11a, 11b and lateral side edge 12b are crossing. The required shape of the notch cut out 13a, 13b will be explained later.

Figure 4:
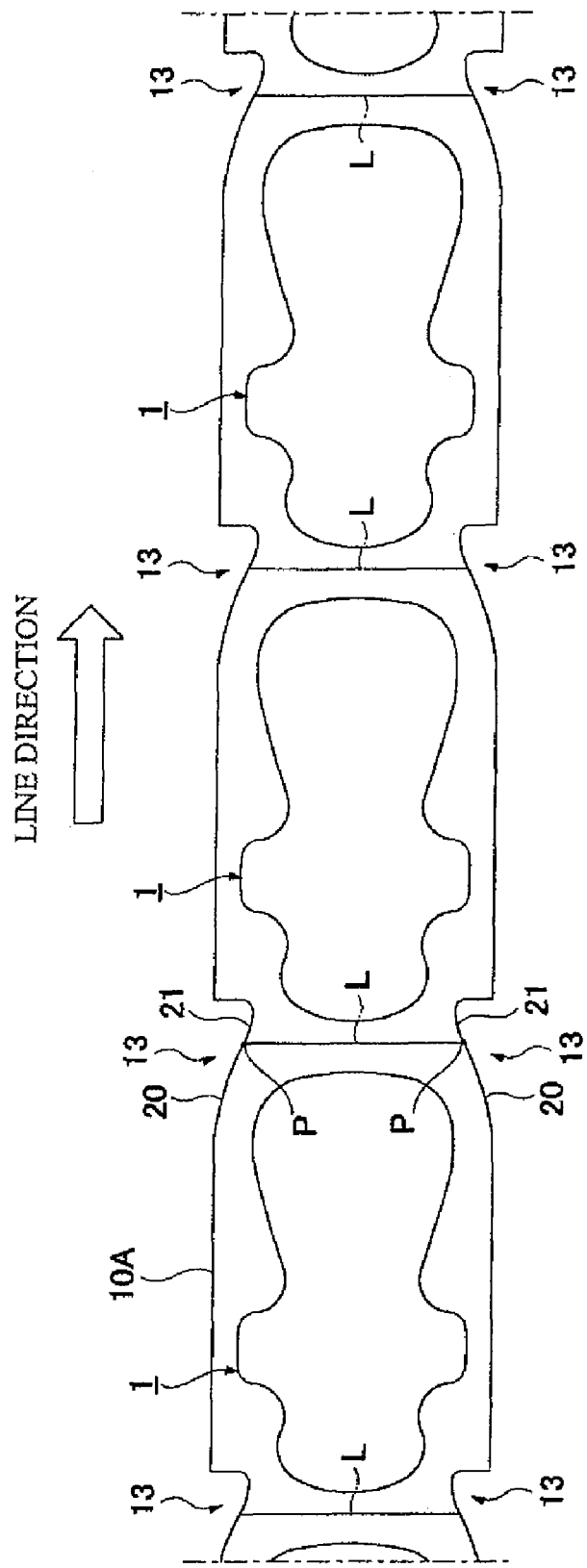
FIG. 4 is a plan view showing the point of the production of the individually packaged absorbent article.

In the production step of the individually packaged absorbent article where the aforementioned sanitary napkin 1 is packed by the package sheet 10, the package sheet 10 runs out as a continuous band shape sheet in the line direction as shown in FIG. 4, and the sanitary napkin 1 is placed at a predetermined interval. Here, the sanitary napkin 1 is placed so that the rear side of the napkin 1 is to be the front to the line direction because of the relation of the cut shape with the band sheet 10A. The production speed (the line speed) of the individually packaged absorbent article is preferably in the range from 50 to 200 m/min in order to avoid the folding back, getting wrinkles and the like. At 50 m/min or less, generation of folding back and getting wrinkles of the package sheet 10 can be suppressed; however, it is not preferable because the productivity decreases.

In the individually packaged absorbent article according to the invention, the notch cut outs 13, 13 are formed satisfying the following conditions in the intermediate section where the napkins 1 are placed at a predetermined interval in the band sheet 10A. Here, in the illustrated example by the figure, said notch cut out 13 is formed in both side sections of the band sheet 10A; however, it is enough that it is formed in the side edge section of at least one side.

Figure 5:
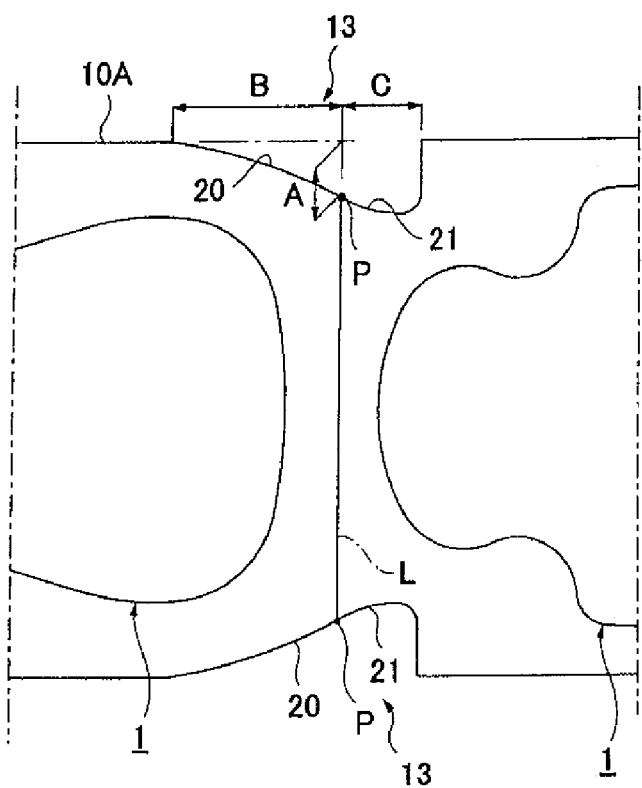
FIG. 5 is an enlarged plan view showing the notch cut out 13.

(1) As the first condition, as shown in the FIG. 5, the notch cut out 13 is formed by the outward curved cut line 20 in a shape bulging to the outside of the band sheet 10 toward the slanted forehand inclined direction of the line front from the cut start point of the side edge section, the inward curved cut line 21 which continues from the terminal end of said outward curved cut line 20 through the inflexion point P, and is in a shape bulging to the inside of the band shape sheet 10A, the cut shape line in a nearly longitudinally half cut drop shape which continues from the inward curved cut line 21, extends to the width direction of the band sheet 10 A and reaches the cut end point of the side edge section.

(2) As the second condition, as shown in FIG. 5, when the sectional distance in the line direction of said outward curved cut line 20 is referred to as B and the distance from said inflexion point P to the side edge line of the band sheet 10A is referred to as A, the condition B>1.5A is to be satisfied.

In addition, the relation between the sectional distance B in the line direction of said outward curved cut line 20 and the sectional distance C in the line direction of the inward curved cut line 21 is preferably C/(B+C)=0.2~0.5. The relational expression indicates the formation position of the inflexion point P. In the example shown in FIG. 5, the inflexion point P and the cutting line L of the individually packaged absorbent article is coincident, however, the position of the inflexion point P can be arbitrarily determined so long as it is within the range of said relational expression.

Figure 6A:
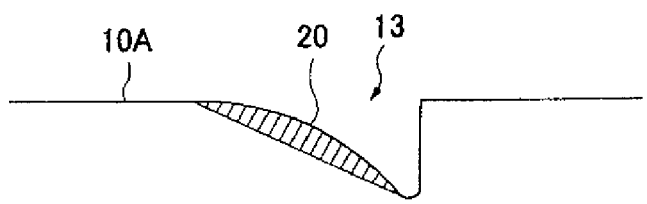
FIGS. 6(A) and 6(B) are enlarged plan views of the notch cut outs 13 which are not the subject of the invention.
Figure 6B:
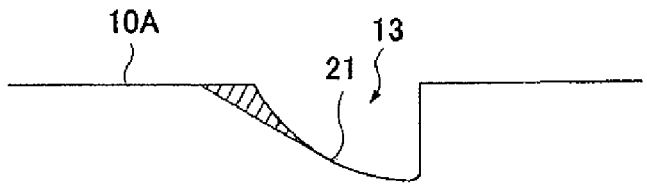
Figure 6C:
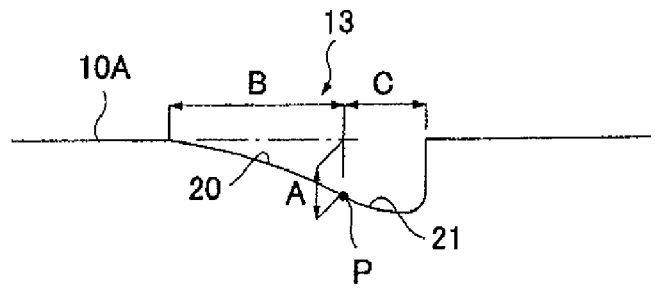
FIG. 6(C) is an enlarged plan view of the notch cut out 13 which is the subject of the invention.

In the invention, the aforementioned problems are solved by the formation of the notch cut out 13 which satisfies the above-mentioned two conditions. For example, as shown in FIG. 6 (A), in the case where the notch cut out 13 is formed by the outward curved cut line 20 alone or as shown in the same FIG. (B) by the inward curved cut line 21 alone, the diagonal line section in the figures is folded or getting wrinkles in the production line. On the contrary, since the cut shape line according to the invention is as shown in the same FIG. (C) to be the combination of the outward curved cut line 20 and the inward curved cut line 21, and is formed in a determined dimension, inconvenience of the individual package such as folding back, wrinkles and the like are not generated in the production line.

Here, said notch cut out 13 is made to be a nearly rectangular sheet defined by the matched pair longitudinal side edges 11a, 11b corresponding to the longitudinal direction of the napkin 1 and the matched pair lateral side edges 12a, 12b corresponding to the lateral direction of the napkin 1 as shown in FIG. 3, through cutting at the cut line L in the intermediate section where the sanitary napkins 1 of the band sheet 10A are placed. At the same time, said notch cut outs 13a, 13a are formed at the corner where the lateral side edge 12a and the longitudinal side edges 11a, 11b are crossing and said notch cut outs 13b, 13b are formed at the corner where the lateral side edge 12b and the longitudinal side edges 11a, 11b are crossing.

Figure 7:
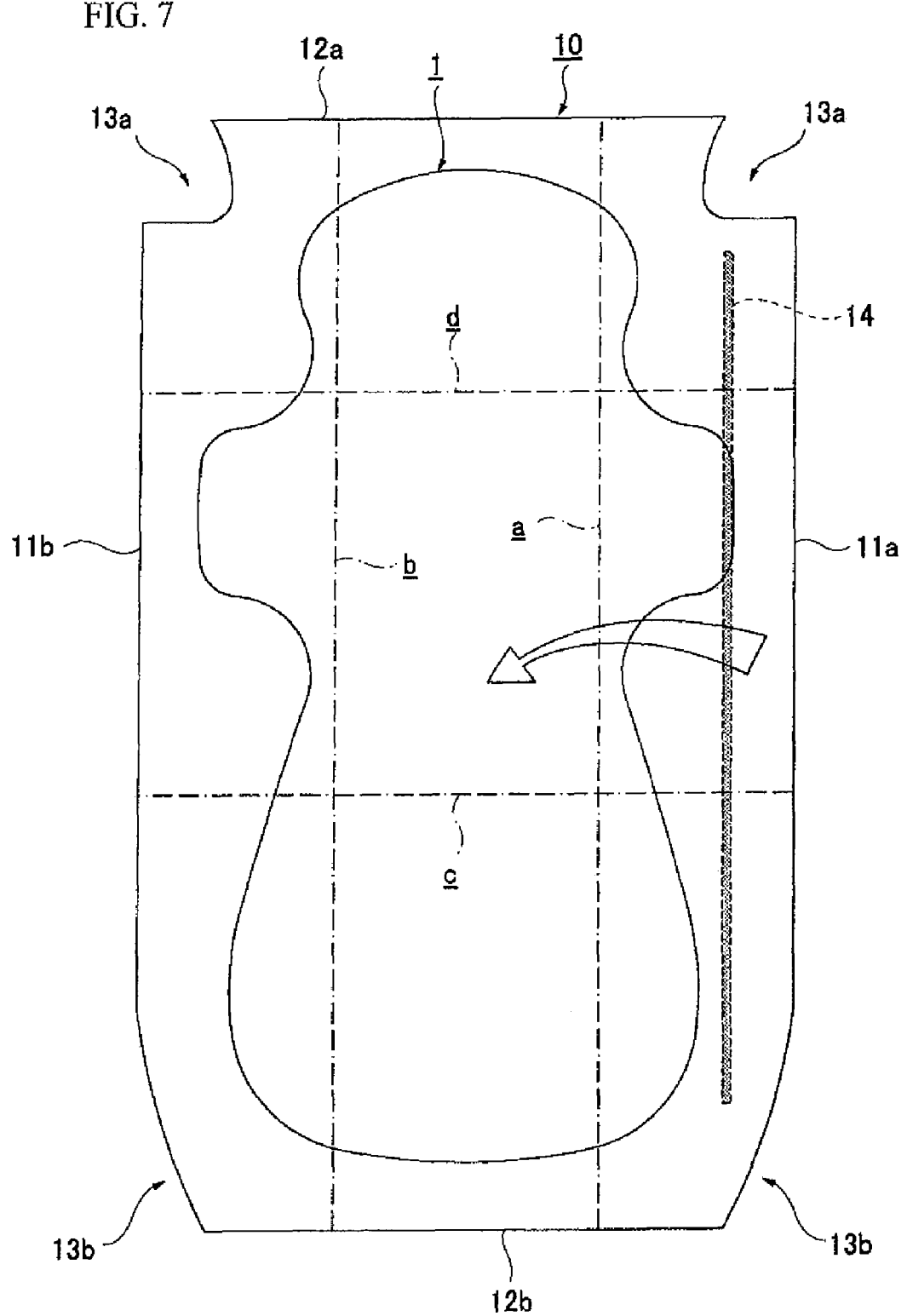
FIG. 7 is a plan view showing the individual packaging procedure (No.1)

In order to individually package aforementioned sanitary napkin 1, as shown in FIG. 7, in the nearly central section on the release treatment processing side of the package sheet 10, the front side of the napkin 1 is placed to be the side of the lateral side edge 12a. Here, the napkin 1 may be placed in a state biased to the longitudinal side edges 11a or 11b side on the one side.

Figure 8:
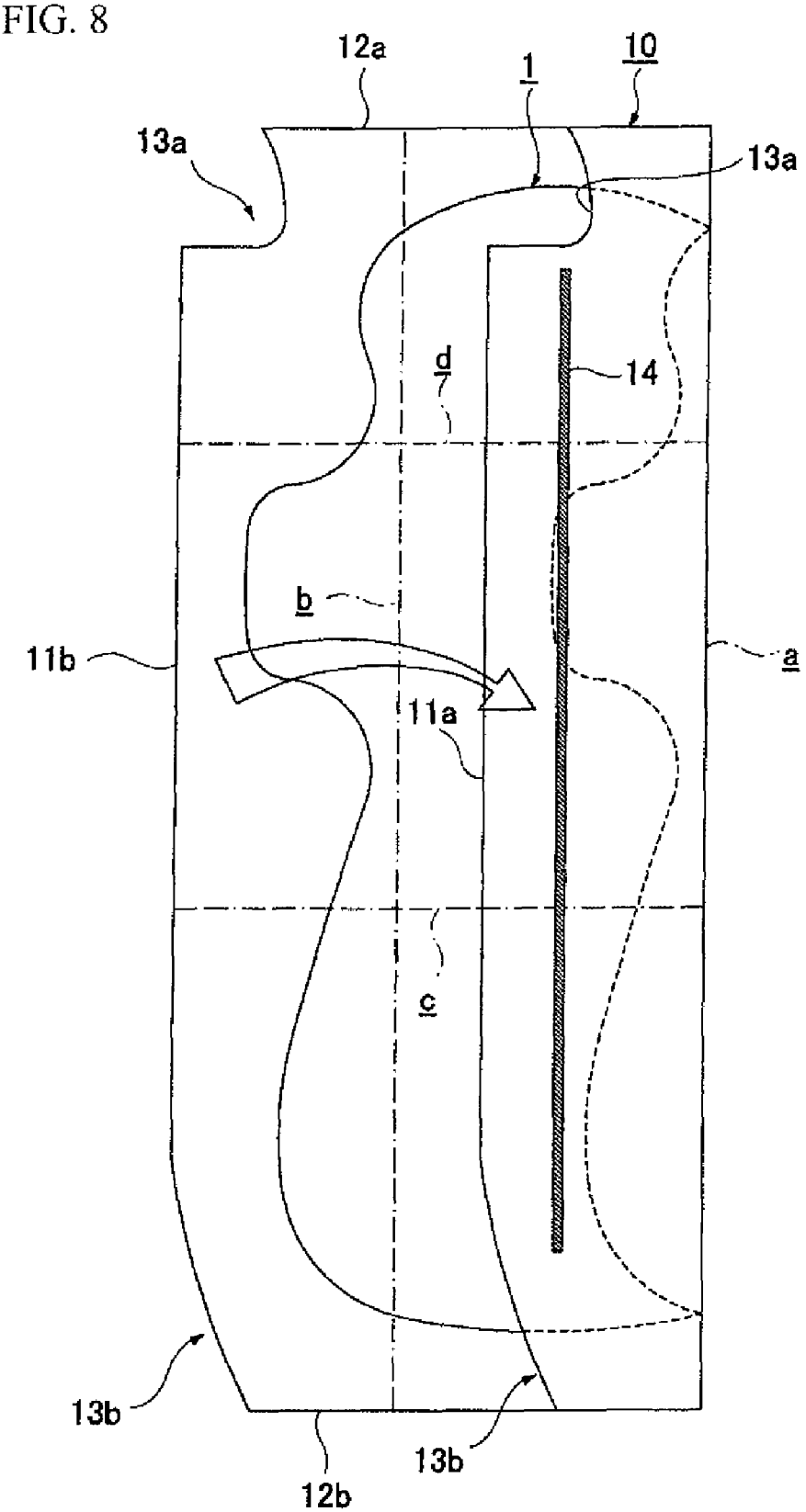
FIG. 8 is a plan view showing the individual packaging procedure (No.2)

From the state shown in FIG. 7, as shown in FIG. 8, firstly, the longitudinal side edge 11a side section on the one side of the package sheet 10 on the side where the line shape adhesive is provided is to be folded to the surface sheet 3 side together with the wing shape flap W at the folding line a positioned in the vicinity of the outside of the side edge of aforementioned absorber 4. Here, as previously mentioned, the position of the folding line a is to be the position in the vicinity of the outside of the side edge of the absorber 4, however, occasionally it is also possible to be the base end section of the wing shape flap W or the second wing shape flap $W_B$ without containing the side section flap of the napkin 1. Alternatively, it may be folded including a part of the absorber side edge.

Next, as shown in the same FIG. 8, the longitudinal side edge 11b side section on the other side of the package sheet 10 is to be folded together with the wing shape flap W and the second wing lap $W_B$ to the surface sheet 3 side at the folding line b. The longitudinal side edge 11b side section on the other side is releasably bonded by the line shape adhesive 14 provided on the outer face of the longitudinal side edge 11a side section on the other side.

Figure 9:
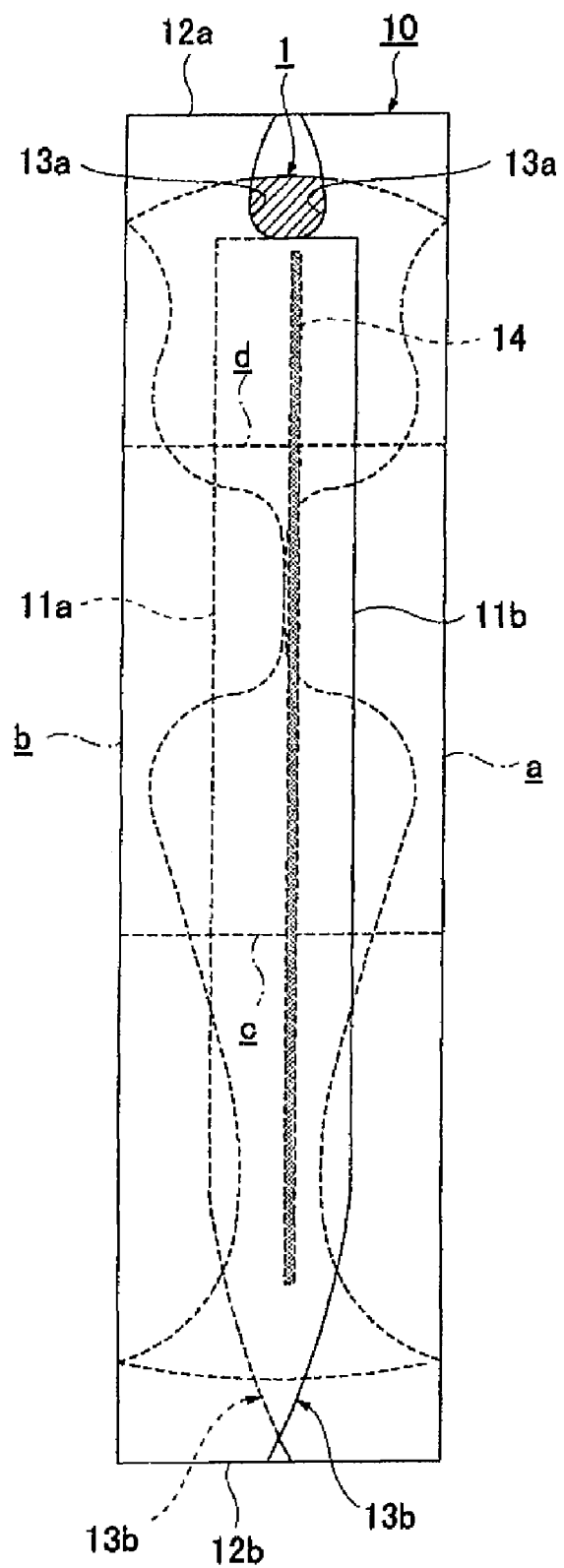
FIG. 9 is a plan view showing the individual packaging procedure (No.3)

As shown in FIG. 9, in a state where both side sections of the longitudinal side edges 11a, 11b of the package sheet 10 is sequentially folded to the liquid-permeable surface sheet 3 side, the front end section (diagonal line section) of the napkin 1 is made to be presented to the outside from the opening section formed by the notch cut outs 13, 13 formed in the package sheet 10. Here, said line shape adhesive 14 is fixed to the longitudinal side edge 11a side on the one side in the product state, however, in the production line, it is preferable to be provided on a face of the release treatment side on the other side longitudinal side edge 11b, and by overlapping the longitudinal side edge 11b to the longitudinal side edge 11a on the one side to be transcribed to the longitudinal side edge 11a side on the one side. Said line shape adhesive 14 may be a continuous or intermittent line shape.

As shown in FIG. 9, in a state where the napkin 1 and the package sheet 10 are folded in the width direction, since the notch cut outs 13a, 13a formed by the cut shape line in a nearly longitudinal half cut drop shape formed in the longitudinal side edges 11a, 11b are placed in an opposing manner, an opening section in a nearly drop shape is formed, and the front end section of the napkin 1 (diagonal line section) is presented to the outside from the opening section.

Figure 10:
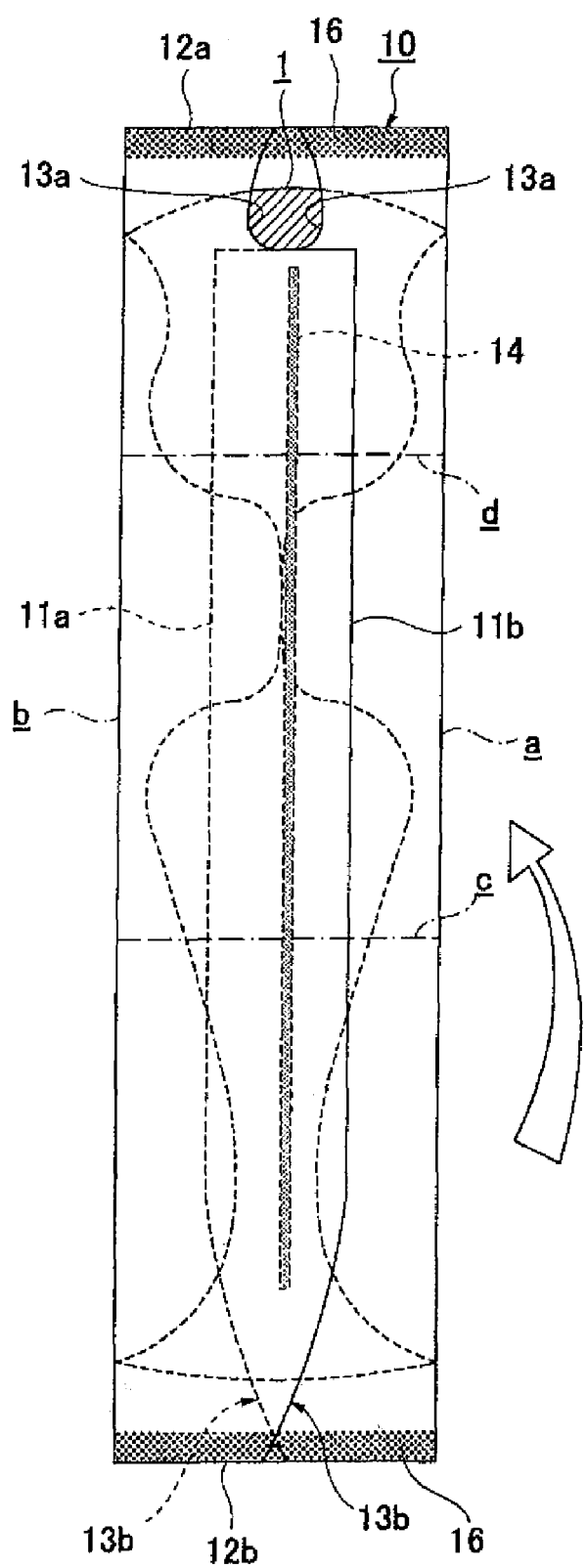
FIG. 10 is a plan view showing the individual packaging procedure (No.4)

If the folding of said napkin 1 and the package sheet 10 in the width direction is completed, as shown in FIG. 10, in both end sections in a longitudinal direction, the heat-sealing 16,16 is applied to the overlapping tab of the package sheet 10, and releasably bonded.

Figure 11:
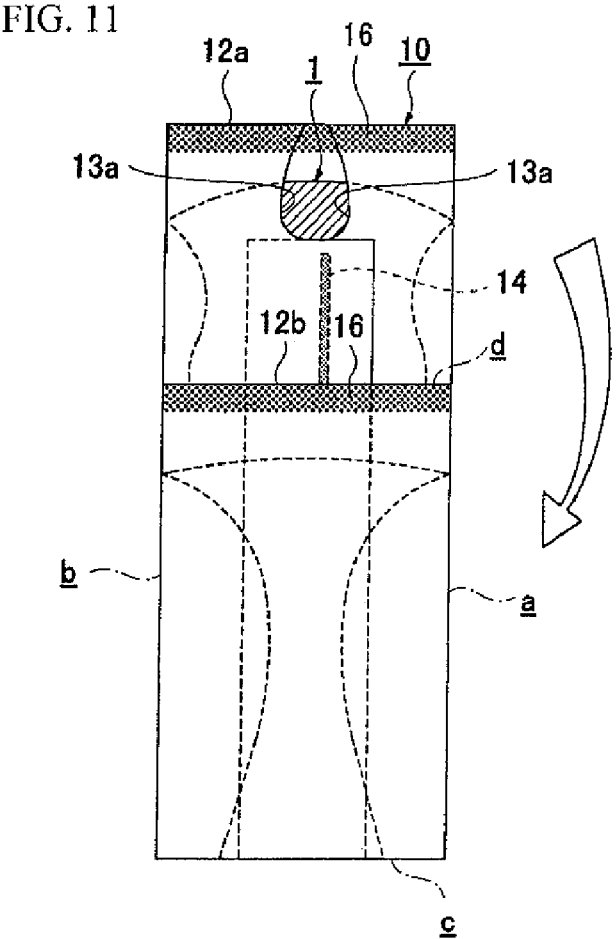
FIG. 11 is a plan view showing the individual packaging procedure (No.5)
Figure 12:
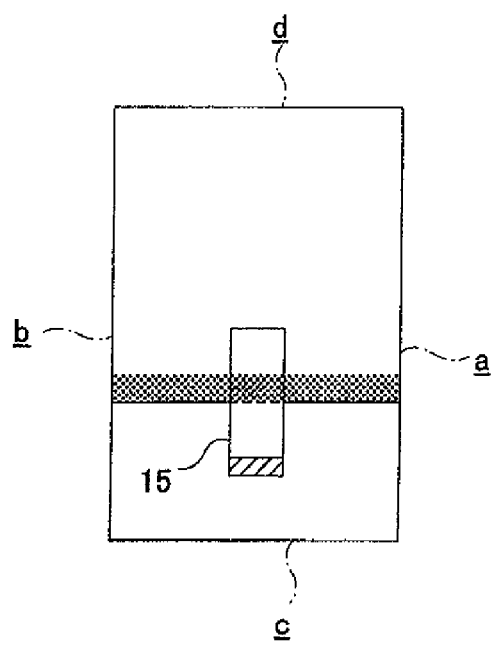
FIG. 12 is a plan view showing the individual packaging procedure (No.6)

In addition, as is shown in the same FIG. 10, in the direction from the end section of the absorber 4 following the lateral side edges 12a, 12b of the package sheet 10, and at the position of the folding line c set at the position near the rear side of the napkin 1 (the position divided at nearly ⅓ of the longitudinal direction), after both the rear side of the napkin 1 and the lateral side edge 12b side section of the package sheet 10 are folded to the surface sheet 3 side (refer to FIG. 11), as shown in FIG. 12, in the direction following the lateral side edges 12a, 12b of the package sheet 10, and at the position of the folding line d set at the position near to the front side of the napkin 1 (the position at nearly ⅓ of the longitudinal direction), the rear side of the napkin 1 and the lateral side edge 12a side section are folded, and the adhesive layer of the tag tape 15 provided on the lateral side 12a is releasably bonded to the outface of the package sheet 10, and the folded shape is held.

At the time of use of these individually packaged absorbent article, bonding of said tag tape 15 is released from the individually packaged state shown in FIG. 12 and the folding in the longitudinal direction of the napkin 1 and the package sheet 10 is released to make a development state shown in FIG. 10, the front end section of the napkin 1 is made to be presented to the outside from the opening section formed by the notch cut outs 13a, 13a, and when the napkin 1 is pulled by clipping the front end section of napkin 1 so as to release it from the package sheet 10, the longitudinal side edge both side sections 11a, 11b are developed, while releasing the line shape adhesive 14 bonding the longitudinal side edge both side sections 11a, 11b of the package sheet 10 together, said napkin 1 is easily take out from the package sheet. Here, when the front end section of the napkin 1 exposed from said opening section is clipped, since the notch cut outs 13a, 13a are formed by the inward curved cut line 21 in a shape bulging to the outside, finger tackle of the package sheet 10 is difficult.

(1) In the above-mentioned embodiment, after sequentially folding the longitudinal side edge both side sections 11a, 11b of the package sheet 10, it was folded in three in a longitudinal direction, however, it may be folded in four or two depending on the size of the napkin.

(2) In the above-mentioned embodiment, the aspect was that the napkin 1 has the wing shape flaps W, W at both side sections; however, it is applicable similarly to the napkin having no wing shape flap.

(3) In the above-mentioned embodiment, the overlapping tab of the package sheet 10 at the front and rear end section was releasably bonded by heat-sealing bonding, this heat-sealing can be also omitted.

Figure 13A:
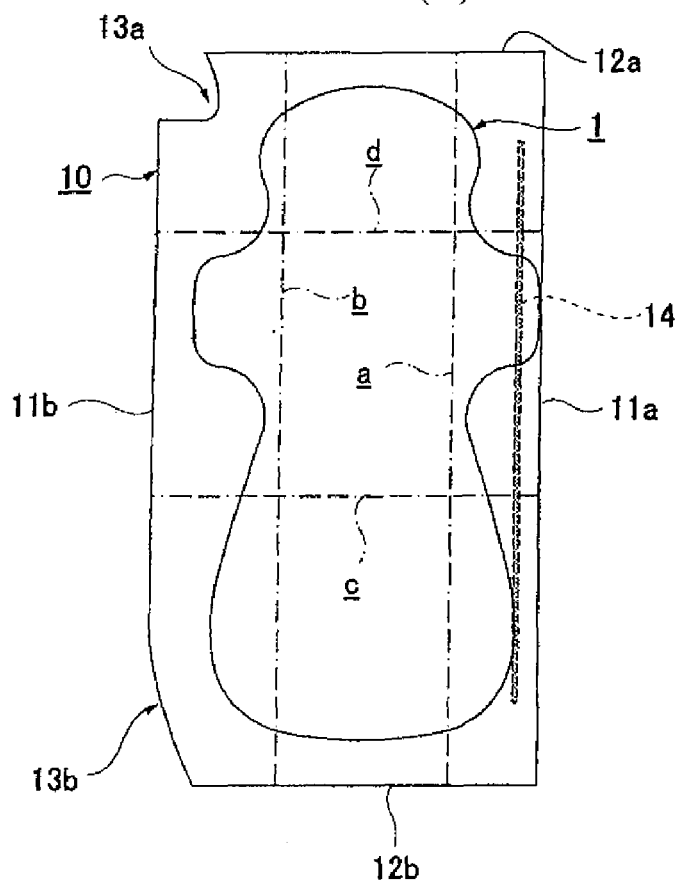
FIGS. 13(A) and 13(B) are plan views showing the individual packaging procedure of the individually packaged absorbent article in another embodiment.
Figure 13B:
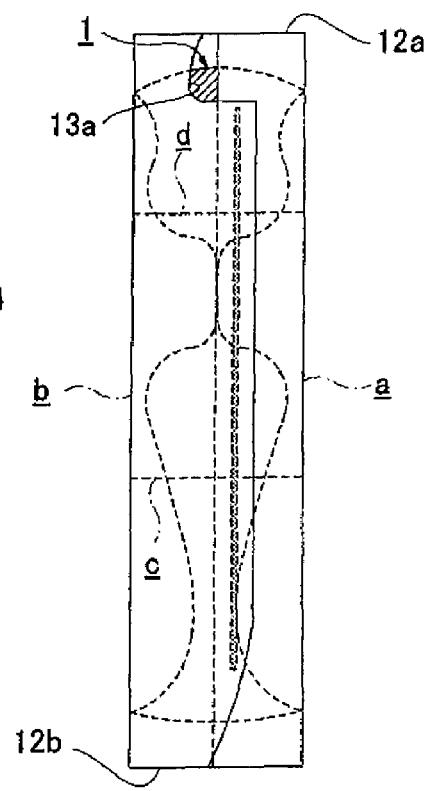
Figure 15:
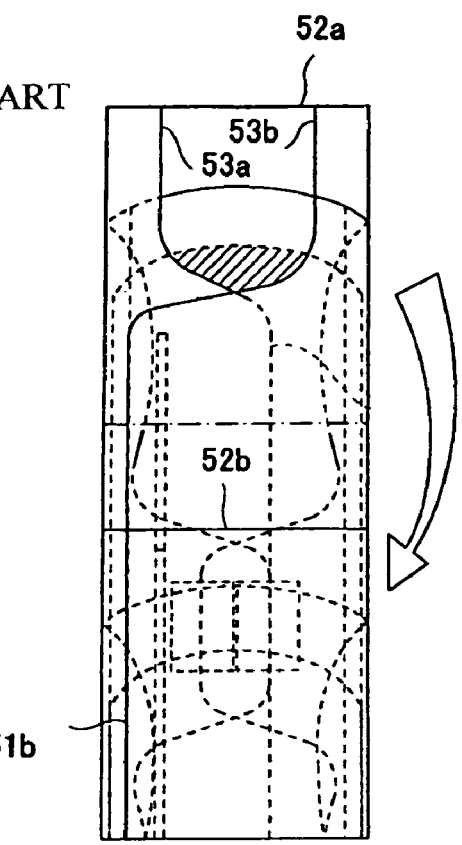
FIG. 15 is a plan view showing the conventional individual packaging procedure (No.1)
Figure 16:
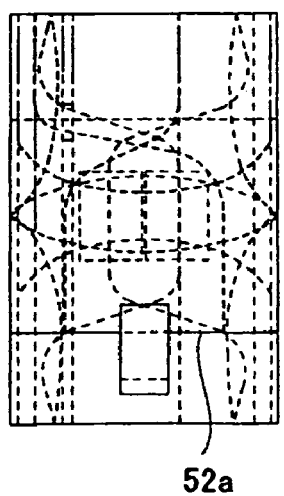
FIG. 16 is a plan view showing the conventional individual packaging procedure (No.2)
Figure 17:
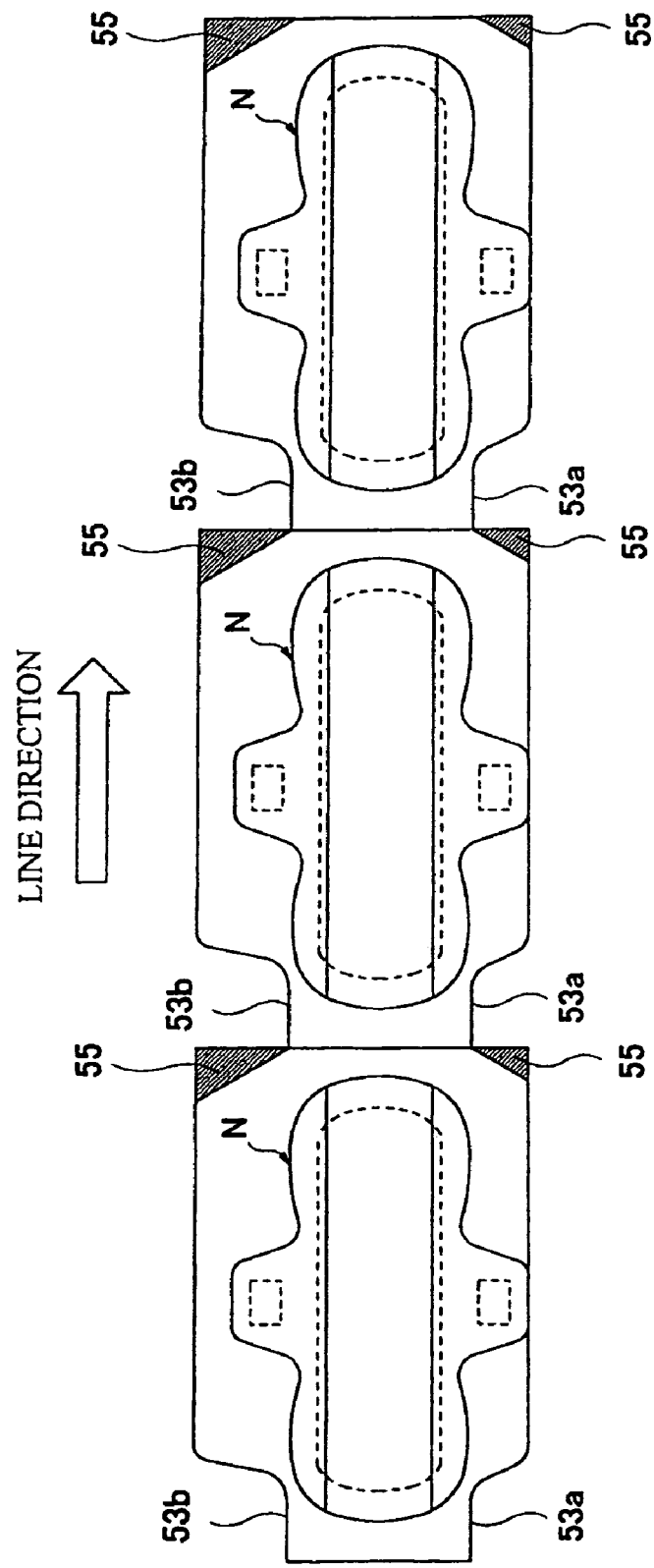
FIG. 17 is a line plan view showing the point of the production of the conventional individually packaged absorbent article.

(4) In the above-mentioned embodiment, the notch cut out 13 is formed at both side edge sections of the band sheet 10A, as shown in FIG. 13, it may be formed on the one side edge section. In this case, as shown in the same FIG. (A), it is preferable to place the napkin 1 biasing to the side where the notch cut out 13 a is not formed against the package sheet 10, and to fold making the width of the fold on the longitudinal side edge 11a side on the side where the notch cut out 13a is not formed. By doing so, as shown in the same FIG. (B), an opening section of a nearly half cut drop shape is formed in a state where the napkin 1 and the package sheet 10 are folded in the width direction, the napkin 1 becomes to be presented to the outside from the opening section. In addition, even in the case where the napkin 1 is not biased on the one side, it is possible to form a nearly half cut drop shape opening section, by decreasing the folding width on the longitudinal side edge 11a side where the notch cut out 13a is not formed or by decreasing the folding width of the longitudinal side edge 11b in the side where the notch cut out 13a is formed.

The invention claimed is:

1. An individually packaged absorbent article comprising, an absorbent article comprising an absorber situated between a liquid-permeable surface sheet and a back face sheet, an adhesive layer, for adhering the absorbent article to a wearer's undergarment, formed on an outer face of said back face sheet, and a package sheet which individually packages the absorbent article, the individually packaged absorbent article being produced by a process comprising forming said package sheet from an elongated continuous band sheet and, at at least one side edge at intermediate sections of the band sheet where the absorbent articles are to be placed at a predetermined interval, forming a notch cut out section which satisfies the following conditions:

(1) said notch cut out section is formed by an outward curved cut line in a shape bulging to the outside of the band sheet toward a slanted forehand inclined direction of a line front from the cut start point of the side edge section, the inward curved cut line which continues from the terminal end of said outward curved cut line through an inflexion point, and is in a shape bulging to the inside of the band sheet, and the cut shaped line is in a nearly longitudinally half cut drop shape which continues from the inward curved cut line, and extends in a width direction of the band sheet to reach a cut terminal point of the side edge;

(2) when the sectional distance in the line direction of said outward curved cut line is referred to as B and the distance from said inflexion point to the side edge of the band sheet is referred to as A, the condition B>1.5A is to be satisfied;

cutting the band sheet into individual package sheets having a matched pair of longitudinal side edges corresponding to the longitudinal direction of the absorbent article and the matched pair lateral side edges parallel to a lateral direction of the absorbent article at a cut line following the width direction of the band sheet from the inside of the section of said outward curved cut line and the inward curved cut line, and providing, on the face of the package sheets which will contact the absorbent article, a release treatment in a region corresponding to at least a region of said adhesive layer, and placing each absorbent article on said face of said package sheet to which said release treatment has been applied, then folding both side sections on the longitudinal side edge side of the package sheet to the liquid-permeable surface sheet whereby a front end section of the absorbent article is made to be presented to the outside from said notch cut out section, and in an overlapping tab section of both side sections of said longitudinal side edge side, releasably bonding both side sections on the longitudinal side edge side by a line of adhesive provided in the longitudinal direction, and then folding together the package sheet and the absorbent article in the longitudinal direction and then sealing the packaged absorbent article with a tab tape.

2. The individually packaged absorbent article according to claim 1, wherein C/B+C)=0.20~0.5 is satisfied, when the sectional distance in the line direction of said outward curved cut line is referred to as B and the sectional distance in the line direction of said inward curved cut line is referred to as C.

3. The individually packaged absorbent article according to any of claim 1, wherein in the absorbent article, a wing shape flap which is protruding toward the side direction from the longitudinal direction side edge section and is fixed in a manner to catch up a crotch section of the undergarment at the time of wearing is provided, and an adhesive layer for preventing displacement of said wing shape flap is provided on the face of the liquid-impermeable back sheet side of the wing shape flap, and when both side sections on the longitudinal side edge side of said package sheet are folded sequentially to the liquid-permeable surface sheet, said wing shape flap is folded to the liquid-permeable surface sheet.

4. The individually packaged absorbent article according to claim 1, wherein said line of adhesive is a continuous line of adhesive or an intermittent line of adhesive.

5. The individually packaged absorbent article according to claim 1, wherein at the stage when said absorbent article is placed on the package sheet, and both side sections on the longitudinal side edge of the package sheet are folded sequentially to the liquid-permeable surface sheet side, heat-sealing is applied in both edge sections in the longitudinal direction.

* * * * *